United States Patent [19]

Stern

[11] Patent Number: 4,507,323

[45] Date of Patent: Mar. 26, 1985

[54] TREATMENT OF PSYCHOSEXUAL DYSFUNCTIONS

[75] Inventor: Warren C. Stern, Raleigh, N.C.

[73] Assignee: Burroughs Wellcome Co., Research Triangle Park, N.C.

[21] Appl. No.: 634,451

[22] Filed: Jul. 25, 1984

[51] Int. Cl.³ .......................................... A61N 31/135
[52] U.S. Cl. .................................................. 514/649
[58] Field of Search ........................................ 424/330

[56] References Cited

U.S. PATENT DOCUMENTS 3,819,706  6/1974  Mehta ................................. 424/330
3,885,046  5/1975  Mehta ................................. 424/330

Primary Examiner—Stanley J. Friedman
Attorney, Agent, or Firm—Donald Brown

[57] ABSTRACT

A method of treatment of pychosexual dysfunction in male and female human beings by the administration of the compound of the formula (I)

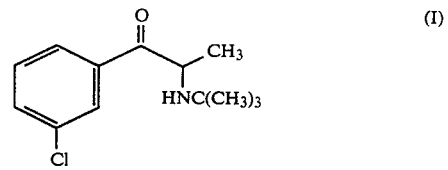

or a pharmaceutically acceptable acid addition salt thereof in a non-toxic, effective therapeutic amount (calculated as base) to a human being in need thereof.

12 Claims, No Drawings

TREATMENT OF PSYCHOSEXUAL DYSFUNCTIONS

BACKGROUND OF THE INVENTION

This invention is directed to a method of treatment of psychosexual dysfunction in human beings by the administration of the compound of the formula (I)

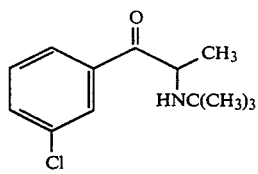

or a pharmaceutically acceptable salt thereof in a nontoxic, therapeutic amount to a human being in need thereof.

Psychosexual dysfunctions which are treated according to this invention are those in which a physical disorder or another AXIS I mental disorder, e.g., major depression, is not the primary cause of disturbance in sexual function. In these situations, a psychosexual dysfunction is not properly diagnosed and this invention is not directed to those conditions in which the primary diagnosis is not psychosexual dysfunction.

The particular psychosexual dysfunctions treatable by the methods disclosed herein are:
1. Inhibited Sexual Desire
2. Inhibited Sexual Excitement
3. Inhibited Female Orgasm
4. Inhibited Male Orgasm
5. Premature Ejaculation
6. Functional Dyspareunia
7. Functional Vaginismus
8. Atypical Psychosexual Dysfunction The diagnosis for each of the conditions and a general background of psychosexual dysfunction is set forth in the text Diagnostic and Statistical Manual of Mental Disorders (Third Edition), American Psychiatric Association, Washington, D.C., APA, 1980, Library of Congress Catalogue Number 79-055868, Copyright American Psychiatric Association, 1980, pages 275 to 283 and in particular paragraphs 302.71, 302.72, 302.73, 302.74, 302.75, 302.76, 306.51 and 302.70 set forth on these pages 278 to 283.

There is no accepted pharmacological treatment of psychosexual dysfunction, currently accepted treatment consisting of various forms of psychotherapy and behavior therapy. The effectiveness of such treatment is quite variable, and since it tends to be both prolonged and expensive it is not accessible to many sufferers. The incidence of psychosexual dysfunction in the United States of America is not known precisely, but it is estimated to be extremely common. In males the incidence increases with age to a level as high as 75% in those over 65 years old.

The compound of formula (I) as its hydrochloride salt has been shown to be effective in treating human psychosexual dysfunction in a placebo-controlled clinical trial and to exhibit few side-effects; however, the biological activity resides in the base and the identity of the acid is of less importance.

In U.S. Pat. Nos. 3,819,706 and 3,885,046, the compound of formula I (chemically named m-chloro-α-t-butylaminopropiophenone) and salts thereof are disclosed as being antidepressants.

The compound of formula (I) (the active ingredient) or a pharmaceutically acceptable salt thereof is preferably administered in unit dosage form to the human being under treatment.

A pharmaceutical composition containing the compound of formula (I), or a pharmaceutically acceptable salt thereof, may be presented in discrete units such as cachets, tablets, capsules, ampules or suppositories, each containing the compound or salt in an effective amount for the treatment of psychosexual dysfunction or an appropriate fraction of such amount.

As an example, for the treatment of human beings having one or more particular types of psychosexual dysfunction, the preferred unit dosage of the compound of formula (I) or salt thereof (calculated as the base) for oral administration or for rectal administration, for example as a suppository, is about 15 milligrams to 500 milligrams, preferably 15 milligrams to 350 milligrams, the most preferred unit dosage being in the range 25 milligrams to 300 milligrams taken two or three times a day. Therapeutic (effective) dosage in humans is preferably 1 to 15 mg/kg (orally) per day. The most preferred unit dose is 135 mg in terms of base taken 2 or 3 times per day. Treatment is given on a continuous basis to a person already diagnosed as having psychosexual dysfunction. All the above doses are expressed in terms of the weight of the compound of formula (I) in the form of its base, but as will be appreciated from the foregoing information, it may be administered in the form of a pharmaceutically acceptable salt thereof. Parenteral administration may be used and in this case the dose would be about one half the above-indicated oral dosage.

The compound of formula (I) or a pharmaceutically acceptable salt thereof may be presented as an oral preparation (for example as a cachet, tablet or capsule) containing in addition one or more pharmaceutically acceptable carriers which may take the form of solid diluents such as lactose, cornstarch, micronized silica gel as well as other excipients known in the art.

It should be understood that in addition to the aforementioned ingredients, the pharmaceutical compositions of this invention may include one or more additional ingredients, e.g., pharmaceutically acceptable carriers such as diluents, buffers, flavouring agents, binders, surface active agents, thickeners, lubricants, preservatives and the like. The formulations may be prepared by admixture of the ingredients and, if necessary, shaping of the resulting mass, and filling into suitable containers.

The compound of formula I is preferably presented for use as a pharmaceutically acceptable salt. Examples of some of the pharmaceutically acceptable salts which can be utilized are salts of the following acids: hydrochloric, sulfuric, phosphoric and toluenesulphonic acids.

Reference should be had to U.S. Pat. Nos. 3,819,706 and 3,885,046, which are incorporated herein by reference thereto for a description of the preparation of the compound of formula (I), salts thereof and tablets, capsules, parenteral solutions and suppositories incorporating same.

EXAMPLE I

The hydrochloride salt of the compound of formula (I) is administered orally as a tablet to a patient identified by a clinician as having the symptoms associated with inhibited sexual desire or other psychosexual dysfunction. The patient is administered a daily dose of 100 mg (calculated as base) in two or three equally divided doses, 6 hours between doses.

The patient is treated continuously for several months and then taken off the drug periodically to determine whether the underlying pathology is resolved. If not, treatment is reinstituted.

I claim:

1. A method of treating psychosexual dysfunction in a human being suffering from same, which comprises administering to said human being an effective, non-toxic, sexual dysfunction therapeutic amount of the compound of the formula (I)

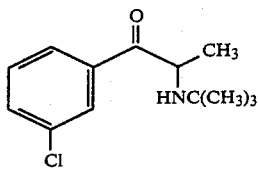

(I)

or a pharmaceutically acceptable salt thereof.

2. The method of claim 1 in which a pharmaceutically acceptable salt is administered.

3. The method of claim 2 in which the salt is the hydrochloride salt.

4. The method of claim 1 in which the compound or salt is administered in a pharmaceutically acceptable carrier therefor.

5. The method of claim 2 wherein said compound or salt is administered in a pharmaceutically acceptable carrier therefor.

6. The method of claim 3 wherein said compound or salt is administered in a pharmaceutically acceptable carrier therefor.

7. The method of claim 1 in which the compound or salt is administered orally.

8. The method of claim 2 wherein said compound or salt is administered orally.

9. The method of claim 3 wherein said compound or salt is administered orally.

10. The method of claim 4 wherein said compound or salt is administered orally.

11. The method of claim 5 wherein said compound or salt is administered orally.

12. The method of claim 6 wherein said compound or salt is administered orally.

* * * * *

UNITED STATES PATENT AND TRADEMARK OFFICE
CERTIFICATE OF CORRECTION

PATENT NO. : 4,507,323

DATED : March 26, 1985

INVENTOR(S) : Warren C. Stern

It is certified that error appears in the above—identified patent and that said Letters Patent is hereby corrected as shown below:

In claims 5, 6, 8, 9, 11 and 12 please delete "compound or".

Signed and Sealed this

Second Day of December, 1986

Attest:

DONALD J. QUIGG

*Attesting Officer*   *Commissioner of Patents and Trademarks*